United States Patent
Kalum et al.

(10) Patent No.: US 9,309,549 B2
(45) Date of Patent: Apr. 12, 2016

(54) METHOD FOR EXTRACTING COMPONENTS FROM A YEAST CELL CULTURE

(75) Inventors: Lisbeth Kalum, Vaerloese (DK); Per Munk Nielsen, Hilleroed (DK); Steffen Ernst, Broenshoej (DK)

(73) Assignee: Novozymes A/S, Bagsvaerd (DK)

( * ) Notice: Subject to any disclaimer, the term of this patent is extended or adjusted under 35 U.S.C. 154(b) by 1902 days.

(21) Appl. No.: 11/745,537

(22) Filed: May 8, 2007

(65) Prior Publication Data

US 2007/0292938 A1    Dec. 20, 2007

Related U.S. Application Data

(60) Provisional application No. 60/810,323, filed on Jun. 2, 2006.

(30) Foreign Application Priority Data

May 10, 2006  (DK) .................................. 2006 00658

(51) Int. Cl.
- *C12N 1/16* (2006.01)
- *C12P 21/06* (2006.01)
- *A23L 1/30* (2006.01)
- *C12N 1/06* (2006.01)
- *C12N 9/18* (2006.01)

(52) U.S. Cl.
CPC ............... *C12P 21/06* (2013.01); *A23L 1/3018* (2013.01); *C12N 1/063* (2013.01); *C12N 9/18* (2013.01)

(58) Field of Classification Search
None
See application file for complete search history.

(56) References Cited

FOREIGN PATENT DOCUMENTS

WO    WO 95/22614    8/1995

OTHER PUBLICATIONS

Halász, et al., Use of yeast biomass in food production, CRC Press, Inc., 1991, pp. 177-181.*
Harris et al., Analytical Biochemistry, vol. 193, Issue 2, Mar. 1991, pp. 191-196.*
Ryan et al., Biotechnology Letters vol. 7 No. 6 409-412 (1985).*
Trivedi et al., Indian Journal of Biochemistry & Biophysics, vol. 19, pp. 336-341 (1982).
Conway et al., Canadian Journal of Microbiology, vol. 47, No. 1, pp. 18-24 (2001).
Verduyn et al., World Journal of Microbiology & Biotechnology, vol. 15, pp. 57-63 (1999).
Ichimasa et al., Agricultural and Biological Chemistry, vol. 49, No. 4, pp. 1083-1090 (1985).
Ryan et al., Biotechnology Letters, vol. 7, No. 6, pp. 409-412 (1985).
Nagodawithana "Savory Flavours", Esteekay Associates, Inc., Wisconsin, USA pp. 240-251 (1995).

* cited by examiner

*Primary Examiner* — Irene Marx
(74) *Attorney, Agent, or Firm* — Kristin McNamara

(57) ABSTRACT

The present invention relates to a method for extracting components from yeast cells with a purified phospholipase.

10 Claims, No Drawings

METHOD FOR EXTRACTING COMPONENTS FROM A YEAST CELL CULTURE

CROSS-REFERENCE TO RELATED APPLICATIONS

This application claims priority or the benefit under 35 U.S.C. 119 of Danish application no. PA 2006 00658 filed May 10, 2006 and U.S. provisional application No. 60/810,323 filed Jun. 2, 2006, the contents of which are fully incorporated herein by reference.

TECHNICAL FIELD

The present invention relates to a method for extracting components from a yeast cell culture with a phospholipase.

BACKGROUND OF THE INVENTION

Yeast cultures are used as a source for extraction of several components. The term "yeast extract" is usually used for a concentrate of soluble material derived from yeast cells that have been subjected to hydrolysis of cell material, particularly proteins, soluble carbohydrates and nucleic acids. Yeast cells can also be used as a source for specific single components which are extracted and purified from yeast cells. These components may be naturally produced by the yeast in question or may be produced by the yeast cells after genetic manipulation. Both when producing yeast extract and when purifying specific components from yeast cell cultures there is a desire to increase the yield of the product of interest to improve the economy of the production. Production of yeast extracts is described on pages 240-251 of Nagodawithana (1995) Savory Flavours, Esteekay Associates, Inc., Wisconsin, USA.

SUMMARY OF THE INVENTION

The inventors have found that treatment of a yeast cell culture with a phospholipase facilitates the extraction of components from the culture. Accordingly, the present invention is related to a method for extracting one or more components from yeast, the method comprising: i) treating yeast cells with a phospholipase; and ii) separating the desired one or more components from the treated yeast cells. In other aspects the invention relates to a method for producing a yeast extract and for use of a purified phospholipase to extract one or more components from a yeast cell culture.

DETAILED DESCRIPTION OF THE INVENTION

Yeast

A yeast cell culture to be used in the method of the invention may be a culture of any yeast, e.g. a strain of *Saccharomyces*, e.g. *S. cerevisiae*, *S. uvarum*; a strain of *Kluyveromyces*, e.g. *K. fragilis* and *K. marxianus*; or a strain of *Candida*, e.g. *C. utilis*. The yeast cell culture may be selected for its production of one or more desired components and/or may have been genetically modified to produce one or more specific components and/or to increase the yield of one or more specific components. Methods for genetic modification of yeast cells, e.g. by insertion of DNA encoding a desired protein component, is well known in the art. The yeast cell culture may be propagated under conditions favourable to the growth of the cell culture and/or favourable to the production of the one or more desired components in a high yield, before being subjected to the method of the invention.

Component to be Extracted

A component to be extracted from yeast by the method of the invention may be any component naturally produced by a yeast or any component produced by a yeast that has been genetically modified to produce the desired component. Components that are producible in yeast include e.g. enzymes; vitamins, e.g. B1, B6 and B12; antibiotics, astaxanthin; polyhydroxyalkanoates; lycopene; beta-carotene; Human Serum Albumin; gamma-deltalactone; and cis-3-hexanol. In one embodiment of the invention a component to be extracted from yeast is a protein, particularly an enzyme, e.g. a lactase. In another embodiment of the invention a component to be extracted from yeast is a non-protein component, e.g. a carbohydrate. In one embodiment of the invention the one or more components to be extracted is a yeast extract, as described below.

Separation

According to the invention the desired one or more components are separated from the yeast cell culture after treatment with a phospholipase. Separation may be achieved by any method known in the art, depending on the specific one or more components to be separated. Separation may e.g. be achieved by centrifugation, filtration, e.g. microfiltration or ultrafiltration; chromatographic techniques, e.g. size exclusion chromatography, ion exchange chromatography, affinity chromatography, hydrophobic interaction chromatography; and/or precipitation, e.g. by addition of a salt such as e.g. ammonium sulphate. Separation may be achieved by a combination of several separation techniques, e.g. centrifugation may be used to remove cell wall fragments, and one or more chromatographic techniques may subsequently be used to separate one or more specific components.

To facilitate separation the yeast cells may be subjected to methods for disrupting the yeast cells before the separation, e.g. homogenisation and/or addition of one or more components that facilitate cell disruption, e.g. sodium chloride, ethyl acetate or isopropanol.

The method of the invention may facilitate the separation of the one or more desired components from a yeast culture, e.g. by reducing the amount of particulate material to be removed. The method may also increase the yield of the one or more desired components compared to similar extraction methods not including treatment with a phospholipase.

Hydrolysis

In one embodiment of the invention the yeast cell culture is subjected to hydrolysis of protein before after or during the treatment with phospholipase. Hydrolysis of protein may be achieved by any method known in the art, e.g. by proteotytic enzymes. Proteolytic enzymes may e.g. be proteolytic enzymes present in the yeast cells and released e.g. by mechanical rupture of the cells, by plasmolysis or autoaysis. One or more purified proteolytic enzymes may also be added to the yeast cell culture. Hydrolysis may be achieved as described below under yeast extracts.

Yeast Extract

In one embodiment of the invention the one or more components to be extracted is a yeast extract. Thus in one embodiment the invention relates to a method for producing a yeast extract, the method comprising: i) treating yeast cells with a purified phospholipase; and ii) subjecting the treated yeast cells to protein hydrolysis; and iii) removing yeast cell components; wherein step ii) is conducted before, after or during step i).

Yeast extract is a concentrate of soluble matter derived from yeast cell cultures after hydrolysis of cell material, especially proteins, soluble carbohydrates and nucleic acids. Yeast extracts are useful in food applications as flavouring agents/ enhancers as well as in promoting microbial growth in industrial fermentations. The value of yeast extracts depend to a high degree on the amount of protein in the extract, there is thus a desire to achieve the highest possible protein yield. The raw material for producing yeast extracts may be any yeast cell culture from any source. Usually, the raw material is either a yeast cell culture grown especially for the production of yeast cell extract or spent brewers yeast that is discarded by breweries after use in brewing. Production of yeast extract is well known in the art. Yeast cultures used for production of yeast extract include e.g. strains of *Saccharomyces*, e.g. *S. cerevisiae, S. uvarum*, strains of *Kluyveromnyces*, e.g. *K. fragilis* and *K. marxianus*, and strains of *Candida*, e.g. *C. utilis*. If spent brewers yeast is used, it is often subjected to debittering to remove bitter flavours, e.g. by washing at pH 8-9, before production of extract.

The hydrotysis is usually carried out as autolysis wherein the yeast cells' own hydrolytic enzymes are utilised for disruption of cells and hydrolysis of cell components. For autolysis pH and temperature are usually controlled to achieve death of the yeast cells without inactivating the internal enzymes. Autolysis may e.g. be carried out at pH 7 at 55-60° C. for 20 hours. The skilled person may choose pH and temperature conditions suitable for the specific yeast culture and the desired flavour characteristics. pH and temperature conditions may also affect the yield of extract achieved. The degree of autolysis may e.g. be measured by the ratio of amino nitrogen (AN) relative to the amount of total nitrogen (TN) in the autolysate. For highly autolysed media an AN/TN ratio of 0.4-0.5 is common.

One or more hydrolytic enzymes may be added to facilitate the hydrolysis. Most common is the addition of protease to increase the rate of protein hydrolysis. Any protease being active under the specific conditions may be used, depending on the desired characteristics of the product. A protease to be used may e.g. be of animal, plant, or microbial origin, e.g. derived from a bacterium or fungus. Proteases that may be added include papain, subtilisin, e.g. Subtilisin Carisberg, or fungal proteases, e.g. derived from a strain of *Aspergillus*, e.g. *A. oryzae*. Examples of commercial proteases useful in the process of the invention include Alcalase® and Flavourzyme®, both available from Novozymes A/S, Bagsvaerd, Denmark. In one embodiment of the invention one or more purified proteases are added to facilitate hydrolysis of protein.

Hydrolysis may also be achieved by plasmolysis wherein a compound is added, e,g, sodium chloride, ethyl acetate or isopropanol, that induces cell death and cell rupture, leading to release of internal hydrolytic enzymes, Autolysis and plasmolysis may be combined, e.g. by adding sodium chloride to the medium after the autolysis process has been allowed for a defined period of time.

Acid hydrolysis may also be used to obtain hydrolysis of yeast cell components. Acid hydrolysis may e.g. be performed by adding hydrochloric acid to a yeast culture, usually the yeast culture will be in the form of a slurry with a solids concentration of 65-80%. Hydrolysis is often carried out at elevated temperatures, e.g. up to around 100° C., and may e.g. be performed in a falling film evaporator. After the required level of amino nitrogen has been reached the hydrolysate may be adjusted to desired pH, e.g. pH 5-7, usually with sodium hydroxide.

After hydrolysis unwanted components, typically unhydrolysed cell fragments, are removed by separation to produce the yeast extract. Separation may be achieved by any suitable method known in the an, typically by centrifugation and/or filtration. The extract may be submitted to pasteurisation to kill any vegetative cells. inactivate enzymes and prevent growth of microbiological contaminants. The extract will usually be concentrated e.g. by evaporation in a falling film evaporator. The concentrate may also be dried, e.g. by spray drying or drum drying, to yield a yeast extract powder. The final product is usually sold as a liquid, paste, or powder.

Phospholipase

A phospholipase used in the process of the present invention include phospholipase $A_1$, phospholipase $A_2$, phospholipase B, phospholipase C, and phospholipase D, and any combination thereof. In the process of the invention a yeast cell culture is treated with a phospholipase, e.g. a single phospholipase; two or more phospholipases, e.g. two phospholipases, including, without limitation, treatment with both type A and B; both type $A_1$ and $A_2$; both type $A_1$ and B; both type $A_2$ and B; both type $A_1$ and C; both type $A_2$ and C; or treatment with two or more different phospholipases of the same type. Included is also treatment with one type of phospholipase, such as $A_1$, $A_2$, B, C, or D.

The phospholipase activity may be provided by enzymes having other activities as well, such as e.g. a lipase with phospholipase activity. The phospholipase activity may e.g. be from a lipase with phospholipase side activity. In other embodiments of the invention the phospholipase enzyme activity is provided by an enzyme having essentially only phospholipase activity and wherein the phospholipase enzyme activity is not a side activity.

Phospholipase $A_1$ is defined according to standard enzyme EC-classification as EC 3.1.1.32.

Official Name: Phospholipase $A_1$.

Reaction catalyzed:
phosphatidylcholine+water<=>2-acylglycerophosphocholine+a fatty acid anion Comment: has a much broader specificity than EC 3.1.1.4.

Phospholipase $A_2$ is defined according to standard enzyme EC-classification as EC 3.1.1.4

Official Name: phospholipase $A_2$.

Alternative Names:phosphatidyloholine 2-acylhydrotase, lecithinase a: phosphatidase: or phosphatidoupase, Reaction catalysed:
phosphatidyicholine+water<=>1-acylglycerophosphocholine+a fatty acid anion Comment: also acts on phosphatidylethanolamine, choline plasmalogen and phosphatides, removing the fatty acid attached to the 2-position.

Phospholipase B is defined according to standard enzyme EC-classification as EC 3.1.1.5.

Official Name: lysophospholipase.

Alternative Names: lecithinase b; lysolecithinase: phospholipase B; or PLB.

Reaction catalysed:
2-lysophosphatidylcholine+water< >glycerophosphocholine+a fatty acid anion Phospholipase C is defined according to standard enzyme EQ-classification as EC 3.1.4.3. Phospholipase C hydrolyses the phosphate bond of phosphatidylcholine and other glycerophospholipids, e.g. phosphatidylethanotamine, yielding diacylglycerol; this enzyme will also hydrolyse the phosphate bonds of sphingomyelin, cardiolipin, choline plasmalogen and ceramide phospholipids.

Reaction with phosphatidylcholine:
phosphatidyicholine+water<=>1,2-diacylglycerol+choline phosphate Phospholipase D is defined according to standard enzyme EC-classification as EC 3.1.4.4. Phospholipase D hydrolyses the phosphate bonds of phospholipids and sphingornyelin to give the corresponding phosphatidic acid, Reaction with phosphatidylcholine: A phosphatidylcholine+water<=>choline+a phosphatidate.

Phospholipase A

Phospholipase A activity, including phospholipase $A_1$, phospholipase $A_2$, and combinations thereof, may be provided by enzymes having other activities as well, such as e.g. a lipase with phospholipase A activity. The phospholipase A activity may e.g. be from a lipase with phospholipase side activity. In other embodiments of the invention phospholipase A enzyme activity is provided by an enzyme having essentially only phospholipase A activity and wherein the phospholipase A enzyme activity is not a side activity.

Phospholipase A may be of any origin, e.g. of animal origin (such as, e.g. mammalian), e.g. from pancreas (e.g. bovine or porcine pancreas), or snake venom or bee venom. Alternatively, phospholipase A may be of microbial origin, e.g. from filamentous fungi, yeast or bacteria, such as the genus or species *Aspergillus*, e.g. *A. niger; Dictyostelium*, e.g. *D. discoideumr; Mucor*, e.g. *M. javanicus, M. mucedo, M. subtilissimus; Neurospora*, e.g. *N. crassa; Rhizomucor*, e.g. *R. pusillus; Rhizopus*, e.g. *R. arrhizus, R. japonicus, R. stolonifer; Sclerotinia*, e.g. *S. libertiana, Trichophyton*, e.g. *T. rubrum; Whetzelinia*, e.g. *W. sclerotiorum: Bacillus*, e.g. *B. megaterium, B. subtilis; Citrobacter*, e.g. *C. freundii; Enterobacter*, e.g. *E. aerogenes, E. cloacae Edwardsiella, E. tarda; Erwinia*, e.g. *E. herbicola; Escherichia*, e.g. *E. coli; Klebsiella*, e.g. *K. pneumoniae; Proteus*, e.g. *P. vulgaris; Providencia*, e.g. *P. stuartii; Salmonella*, e.g. *S. typhimurium; Serratia*, e.g. *S. liquefasciens, S. marcescens; Shigella*, e.g. *S. flexneri; Streptomyces*, e.g. *S. violaceoruber; Yersinia*, e.g. *Y. enterocolitica*. Thus, phospholipase A may be fungal, e.g. from the class Pyrenomycetes, such as the genus *Fusarium*, such as a strain of *F. culmorum, F. heterosporum. F, solani*, or a strain of *F. oxysporum*. Phospholipase A may also be from a filamentous fungus strain within the genus *Aspergillus*, such as a strain of *Aspergillus awamori, Aspergillus foetidus, Aspergillus japonicus, Aspergillus niger* or *Aspergillus oryzae*. A preferred phospholipase A is derived from a strain of *Fusarium*, particularly *F. venenatum* or *F. oxysporum*, e.g. from strain DSM 2672 as described in WO 98/26057, especially described in claim 36 and SEQ ID NO. 2 of WO 98/26057. Another preferred phospholipase A is PLA2 from *Streptomyces*, such as e.g. PLA2 from *S. violaceoruber*. In further embodiments, the phospholipase is a phospholipase as disclosed in WO 00/32758 (Novozymes A/S, Denmark).

The activity of a phospholipase type A may e.g. be expressed in Lecitase Units (LEU). Phospholipase activity in Lecitase Units is measured relative to a phospholipase standard using lecithin as a substrate. Phospholipase A catalyzes the hydrolysis of lecithin to lyso-lecithin and a free fatty acid. The liberated fatty acid is titrated with 0.1 N sodium hydroxide under standard conditions (pH 8.00; 40,00° C.±0.5). The activity of phospholipase A is determined as the rate of sodium hydroxide consumption during neutralization of the fatty acid and is expressed in Lecitase units (LEU) relative to a Lecitase (phospholipase) standard (available from Novozymes A/S, Bagsvaerd, Denmark). 1 LEU is defined as the amount of enzyme that under standard conditions (pH 8.00; 40.00° C.±0.5) results in the same rate of sodium hydroxide consumption (µmol/min) as the Lecitase standard diluted to a nominal activity of 1 LEU/g.

Phospholipase B

The term "phospholipase B" used herein in connection with an enzyme of the invention is intended to cover an enzyme with phospholipase B activity.

The phospholipase B activity may be provided by enzymes having other activities as well, such as e.g. a lipase with phospholipase B activity. The phospholipase B activity may e.g. be from a lipase with phospholipase B side activity. In other embodiments of the invention the phospholipase B enzyme activity is provided by an enzyme having essentially only phospholipase B activity and wherein the phospholipase B enzyme activity is not a side activity. In one embodiment of the invention, the phospholipase B is not lipases having phospholipase B side activity as defined in WO 98/26057.

The phospholipase B may be of any origin, e.g. of animal origin (such as, e.g. mammalian), e.g. from liver (e.g. rat liver). Alternatively, the phospholipase B may be of microbial origin, e.g. from filamentous fungi, yeasts or bacteria, such as the genus or species *Aspergillus*, e.g. *A. foetidus. A. fumigatus, A. nidulans, A. niger, A. oryzae. Botryteis* e.g. *B. cinerea; Candida*, e.g. *C. albicans; Cryptococcus*, e.g. *C. neoformans, Escherichia*, e.g. *E. coli, Fusarium*, e.g. *F. sporotrichioides, F. venenatum, F. verticillioides; Hyphozyma; Kluyveromyces*, e.g. *K. lactis; Magnapone*, e.g. *M. grisea; Metarhizium*, e.g. *M. anisopliae; Mycosphaerelia*, e.g. *M. graminicola; Neurospora*, e.g. *N. crassa; Penicilium*, e.g. *P. notatum; Saccharomyces*, e.g. *S. cerevislae: Schizosaccharomyces*, e.g. *S. pombe; Torulaspora*, e.g. *T. delbrueckii; Vibrio*; e.g. *V. cholerae*. A preferred phospholipase B is derived from a strain of *Aspergillus*, particularly phospholipase LLPL-1 or LLPL-2 from *A. niger*, e.g. as contained in the *Escherichia coli* clones DSM 13003 or OSM 13004, or phospholipase LLPL-1 or LLPL-2 from *A. oryzae*, e.g. as contained in the *E. coli* clones DSM 13082 or DSM 13083 as described in WO 01/27251, especially described in claim 1 and SEQ ID NOs. 2, 4, 6 or 8 of WO 01/27251.

Phospholipase C

The phospholipase C activity may be provided by enzymes having other activities as well, such as e.g. a lipase with phospholipase C activity or a phosphatase with phospholipase C activity The phospholipase C activity may e.g. be from a lipase with phospholipase C side activity. In other embodiments of the invention the phospholipase C enzyme activity is provided by an enzyme having essentially only phospholipase C activity and wherein the phospholipase C enzyme activity is not a side activity.

The phospholipase C may be of any origin, e.g. of animal origin, such as mammalian origins of plant origin, or of microbial origin, such as fungal origin or bacterial origin, such as from a strain of *Mycobacterium*, e.g. *M. tuberculosis* or *M. bovis*; a strain of *Bacillus*, e.g. *B. cereus*; a strain of *Clostridium*, e.g. *C. bifermentans, C. haemolyticutm, C. novyi, C. sordellii*, or *C. perfringens*; a strain of *Listeria*, e.g. *L. monocytogenes*; a strain of *Pseudomonas*, e.g. *P. aeruginosa*; or a strain of *Staphylococcus*, e.g. *S. aureus*, or a strain of *Burkholderia*, e.g. *B. pseudomallei*.

Phospholipase D

The phospholipase D activity may be provided by enzymes having other activities as well, such as e.g. a lipase with phospholipase D activity, a phosphatase with phospholipase D activity, or a cholinesterase with phospholipase D activity. The phospholipase D activity may e.g. be from a lipase with phospholipase D side activity. In other embodiments of the invention the phospholipase D enzyme activity is provided by an enzyme having essentially only phospholipase D activity and wherein the phospholipase D enzyme activity is not a side activity.

The phospholipase D may be of any origin, e.g. of animal origin, such as mammalian origin, e.g. from mouse, rat, or Chinese hamster; of plant origin, e.g. from cabbage, maize, rice, castor bean, tobacco, cowpea, or *Arabidopsis thaliana*; or of microbial origin, such as of bacterial origin, e.g. from a strain of *Corynebacterium*, e.g. *C. pseudotuberculosis, C.*

*ulcerans*, or *C. haemolyticum*; or fungal origin, such as e.g. from a strain of *Streptomyces*, e.g. *S. antibioticus* or *S. chromofuscus*; a strain of *Trichoderma*, e.g. *T. reesei*; a strain of *Sacoharomyces*, e.g. *S. cerevisiae*; or a strain of *Aspergillus*, e.g. *A. oryzae, A. niger, A. nidulans* or *A. fumigatus*.

Enzyme Sources and Formulation

The phospholipase used in the process of the invention may be derived or obtainable from any of the sources mentioned herein. The term "derived" means in this context that the enzyme may have been isolated from an organism where it is present natively, i.e. the identity of the amino acid sequence of the enzyme are identical to a native enzyme. The term "derived" also means that the enzymes may have been produced recombinantly in a host organism, the recombinant produced enzyme having either an identity identical to a native enzyme or having a modified amino acid sequence, e.g. having one or more amino acids which are deleted, inserted and/or substituted, i.e. a recombinantly produced enzyme which is a mutant and/or a fragment of a native amino acid sequence. Within the meaning of a native enzyme are included natural variants. Furthermore, the term "derived" includes enzymes produced synthetically by e.g. peptide synthesis. The term "denved" also encompasses enzymes which have been modified e.g. by glycosylation, phosphoryation etc. whether in vivo or in vitro. The term "obtainable" in this context means that the enzyme has an amino acid sequence identical to a native enzyme. The term encompasses an enzyme that has been isolated from an organism where it is present natively, or one in which it has been expressed recombinantly in the same type of organism or another, or enzymes produced synthetically by e.g. peptide synthesis. With respect to recombinantly produced enzyme the terms "obtainable" and "derived" refers to the identity of the enzyme and not the identity of the host organism in which it is produced recombinantly.

Accordingly, the phospholipase may be obtained from a microorganism by use of any suitable technique. For instance, a phospholipase enzyme preparation may be obtained by fermentation of a suitable microorganism and subsequent isolation of a phosphouipase preparation from the resuming fermented broth or microorganism by methods known in the art. The phosphotipase may also be obtained by use of recombinant DNA techniques. Such method normally comprises cultivation of a host cell transformed with a recombinant DNA vector comprising a DNA sequence encoding the phospholipase in question and the DNA sequence being operationally linked with an appropriate expression signal such that it is capable of expressing the phospholipase in a culture medium under conditions permitting the expression of the enzyme and recovering the enzyme from the culture. The DNA sequence may also be incorporated into the genome of the host cell. The DNA sequence may be of genomic, cDNA or synithetic origin or any combinations of these, and may be isolated or synthesized in accordance with methods known in the art.

Suitable phospholipases are available commercially. Examples of commercial enzymes are e.g. Lecitase® (Novozymes A/S, Bagsvaerd, Denmark), YieldMAX® (Novozymes A/S, Bagsvaerd, Denmark and Chr. Hansen A/S, Hørsholm, Denmark), Lysomax® (Genencor International, Inc., Palo Alto, Calif.) or Purifine™ (Diversa Corp., San Diego, Calif.). A suitable phospholipase B is e.g. *Aspergillus niger* phospholipase LLPL-2 that can be produced recombinantly in *A. niger* as described in WO 01/27251.

In the process of the invention the phospholipase is a purified phospholipase. The term "purified" as used herein covers phospholipase enzyme preparations wherein components from the organism from which it is derived has been removed. The term "purified" also covers phospholipase enzyme protein free from components from the native organism from which it is obtained, this is also termed "essentially pure" phospholipase and may be particularly relevant for phospholipases which are naturally occurring and which have not been modified genetically, such as by deletion, substitution or insertion of one or more amino acid residues.

Accordingly, the phospholipase is purified, viz. only minor amounts of other proteins being present. The expression "other proteins" relate in particular to other enzymes. The term "purified" as used herein also refers to removal of other components, particularly other proteins and most particularly other enzymes present in the cell of origin of the phospholipase. The phospholipase may be "substantially pure", i.e. free from other components from the organism in which it is produced, i.e., e.g., a host organism for recombinantly produced phospholipase. Preferably, the enzymes are at least 75% (w/w) pure, more preferably at least 80%. 85%, 90% or even at least 95% pure. In a still more preferred embodiment the phospholipase is an at least 98% pure enzyme protein preparation.

The terms "phospholipase" includes whatever auxiliary compounds that may be necessary for the catalytic activity of the enzyme, such as, e.g. an appropriate acceptor or cofactor, which may or may not be naturally present in the reaction system.

The phospholipase may be in any form suited for the use in question, such as e.g. in the form of a dry powder or granulate, a non-dusting granulate, a liquid, a stabilized liquid, or a protected enzyme. Granulates may be produced, e.g. as disclosed in U.S. Pat. No. 4,106,991 and U.S. Pat. No. 4,661,452, and may optionally be coated by methods known in the art. Liquid enzyme preparations may, for instance, be stabilized by adding stabilizers such as a sugar, a sugar alcohol or another polyol, lactic acid or another organic acid according to established methods. Protected enzymes may be prepared according to the method disclosed in EP 238216, Treatment with Phospholipase According to the invention yeast cells are treated with a purified phospholipase. The treatment may be conducted by any appropriate method, e.g. by adding the phospholipase to the yeast cell culture. The yeast cell culture may e.g. be suspended in water when treated with a phospholipase. The treatment with a phospholipase may be conducted before, after or simultaneously with subjecting the yeast cell culture to protein hydrolysis.

Suitable conditions under which to perform the treatment of phosphouipase can be found by the skilled person by usual methods known in the an for optimising enzymatic reactions. The skilled person will know how to adjust parameters such as pH, temperature, and amount of phospholipase to achieve the desired results. In one embodiment of the invention treatment with phospholipase is conducted at a pH between pH 2 and pH 10, such as between pH 3 and pH 9, between pH 2 and pH 6, or between pH 4 and pH 6. The amount of phospholipase to be used in the method of the invention may depend on the activity of the specific phospholipase. When a phospholipase A is used the amount of phospholipase may e.g. be between 0.001 and 1 mg enzyme protein/g dry matter, such as e.g. between 0.005 and 0.1 mg enzyme protein/g dry matter. In one embodiment of the invention a phospholipase is added in an amount sufficient to achieve an increased yield of the one or more components to be extracted compared to a similar extraction process wherein no treatment with a phospholipase takes place. The yield may e.g. be increased by at least 1%, such as at least 2%, at least 5%, at least 10%, or at least 20%.

In one embodiment, the invention relates to use of a punrfied phospholipase, e.g. a phospholipase $A_1$, for extracting one or more components from a yeast cell culture.

EXAMPLES

Example 1

A block yeast cell culture of *Saccharomyces cerevisia* was mixed with de-ionized water to reach a dry matter content of 14% and was stirred by a magnetic stirrer for 60 min at room temperature. The amount of nitrogen in this yeast mixture was determined by a combustion method on a Leco FP-528. Dry solids are measured in the yeast mixture by weighing (after drying at 105° C.). The yeast mixture was heated to 55° C. and pH adjusted to 6.5 with 4N NaOH. Samples were treated with 0.25% (weight/weight of yeast dry matter) of a phospholipase (Lecitase® Ultra, 10 kLU/g Novozymes A/S, Denmark) and/or a 0.5% (weight/weight of yeast dry matter) of a proteolytic enzyme (Alcalase® 2.4 L. Novozymes A/S, Denmark), Enzymes were added to the yeast mixture after ten minutes preheating at 55°. A control sample (blank) was not treated with enzyme. Autolysis was carried out for 22 hours at 55° C. under magnetic stirring. 20 ml samples were taken out and the exact amount was weighed. The samples were inactivated for 85° C. for 10 min. After inactivation the samples were centrifuged for 10 min at 3500 rpm using Multifuge 3S—R from Heraeus. The amount of extract was weighed after decantation. Dry solids were measured in the extract by weighing (after drying at 105° C.) The amount of nitrogen in the extract was determined by a combustion method on a Leco FP-528. The amount of protein was calculated as 6.25 times the amount of nitrogen. Free amino nitrogen was determined using an OPA (o-phthaldialdehyde) method. Based on the above measurements the following was calculated;

% Extract Yield=(g extract after centrifugation)/(g yeast mixture before centrifugation)*100

% Protein Yield=(g extract after centrifugation*Protein content in extract)/(g yeast mixture before centrifugation*protein content of yeast mixture)*100

Degree of hydrolysis=(Number of peptide bonds cleaved/total number of peptide bonds)*100=(h/htot)*100

Where h is expressed as a function of meqv serine NH2: h=(serine NH2-0.4)/1; and htot=7.8. Serine NH2 was measured relative to serine standard containing 100 mg/L by measuring absorption at 340 nm.

The results based on double determinations are shown in table 1

TABLE 1

| Enzyme | % Protein yield | % Extract yield | Degree of hydrolysis |
| --- | --- | --- | --- |
| Blank | 21.2 | 62.1 | 33.9 |
| 0.5% Alcalase 2.4 L | 59.2 | 60.9 | 66.9 |
| 0.25% Lecitase Ultra | 21.8 | 61.8 | 35.7 |
| 0.5% Alcalase 2.4 L 0.25% Lecitase Ultra | 67.4 | 66.8 | 61.1 |

Example 2

Yeast extract was prepared by the same method as in example 1, except that a different phosphotipase was used (YieldMax®, Chr. Hansen A/S and Novozymes A/S, Denmark), and the enzymatic treatment was performed at 40° C. and pH 6.0. The results are given in table 2 (single determinations).

TABLE 2

| Enzyme | % Protein yield | % Extract yield | Degree of hydrolysis |
| --- | --- | --- | --- |
| Blank | 13.9 | 64.0 | 36.6 |
| 0.5% Alcalase 2.4 L | 15.2 | 64.7 | 41.5 |
| 0.5% YieldMax | 13.4 | 63.7 | 37.3 |
| 0.5% Alcalase 2.4 L 0.5% YieldMax | 24.0 | 64.4 | 29.6 |

Example 3

A block yeast cell culture of *Saccharomyces cerevisia* was mixed with de-ionized water to reach a dry matter content of 14% and was stirred by a magnetic stirrer for 60 min at room temperature. The amount of nitrogen in this yeast mixture was determined by a combustion method on a Leco FP-528. Dry solids were measured in the yeast mixture by weighing (after drying at 105° C.). The yeast mixture was heated to 55° C. and either applied at the natural pH (about 5-5.3) or adjusted to 5.8 with 4N NaOH, Samples were treated with 0.25% (weight/weight of yeast dry matter) of a phospholipase (Lecitase® Ultra, 10 kLU/g Novozymes A/S, Denmark) and/or a 0.3% (weight/weight of yeast dry matter) of a proteolytic enzyme (Papain, Pang Bo Biological Co. Ltd)). Enzymes were added to the yeast mixture after ten minutes preheating at 55° C. A control sample (blank) was not treated with enzyme. Autolysis was carried out for 22 hours at 55° C. under magnetic stirring. 30 ml samples were taken out and the exact amount was weighed. The samples were inactivated for 85° C. for 10 min. After inactivation the samples were centrifuged for 10 min at 3500 rpm using Multifuge 3S-R from Heraeus. Analysis of extracts as described in example 1. Turbidity was determined using a Turbidimeter 2100AN from HACH.

The results based on double determinations are shown in table 3.

TABLE 3

| Enzyme | pH in hydrolysate | % Protein yield | % Extract yield | Degree of hydrolysis | Turbidity (NTU) |
| --- | --- | --- | --- | --- | --- |
| Control | 5 | 47.2 | 66.7 | 48.6 | 3820 |
| 0.25% Lecitase Ultra | 5 | 52.5 | 65.9 | 45.9 | 1421 |
| pH adjusted control | 5.8 | 24.8 | 64.5 | 44.3 | 1579 |
| 0.25% Lecitase Ultra | 5.8 | 26.1 | 64.6 | 47.93 | 1449 |
| 0.3% Papain | 5.8 | 63.5 | 68.8 | 71.8 | 2179 |
| 0.3% Papain and 0.25% Lecitase Ultra | 5.8 | 66.5 | 67.3 | 67.8 | 157 |

The invention claimed is:

1. A method for producing a yeast extract, the method comprising:
   i) treating yeast cells with a purified phospholipase A1 in an amount of between 0.001 and 1 mg enzyme protein/g dry matter;
   ii) subjecting the treated yeast cells to protein hydrolysis comprising autolysis and comprising adding one or more proteolytic enzymes to the yeast cells; and
   iii) separating a yeast extract from the treated yeast cells; wherein step ii) is conducted before, after or during step i).

2. The method of claim 1, wherein phospholipase A1 is added in an amount of between 0.005 and 0.1 mg enzyme protein/g dry matter.

3. The method of claim 1, wherein protein hydrolysis further comprises plasmolysis.

4. The method of claim 1, further comprising disrupting the yeast cells before the separation.

5. The method of claim 4, comprising homogenisation and/or addition of one or more components that facilitate cell disruption.

6. The method of claim 4, comprising adding sodium chloride, ethyl acetate or isopropanol.

7. The method of claim 1, further comprising treating yeast cells with a phospholipase A2.

8. The method of claim 1, further comprising treating yeast cells with a phospholipase B.

9. The method of claim 1, further comprising treating yeast cells with a phospholipase C.

10. The method of claim 1, further comprising treating yeast cells with a phospholipase D.

* * * * *